United States Patent
Guo et al.

(10) Patent No.: US 12,333,411 B2
(45) Date of Patent: Jun. 17, 2025

(54) PHOTOELECTRIC DETECTION MODEL TRANSFER AND SHARING METHOD AND INTERNET OF THINGS MONITORING AND EVALUATION SYSTEM BASED ON CLOUD SERVICE

(71) Applicant: JIANGSU UNIVERSITY, Zhenjiang (CN)

(72) Inventors: Zhiming Guo, Zhenjiang (CN); Junyi Wang, Zhenjiang (CN); Xiaobo Zou, Zhenjiang (CN); Jianrong Cai, Zhenjiang (CN); Jiyong Shi, Zhenjiang (CN); Limei Yin, Zhenjiang (CN)

(73) Assignee: JIANGSU UNIVERSITY, Zhenjiang (CN)

( * ) Notice: Subject to any disclaimer, the term of this patent is extended or adjusted under 35 U.S.C. 154(b) by 0 days.

(21) Appl. No.: 18/286,232

(22) PCT Filed: Dec. 20, 2022

(86) PCT No.: PCT/CN2022/140211
§ 371 (c)(1),
(2) Date: Oct. 10, 2023

(87) PCT Pub. No.: WO2024/113434
PCT Pub. Date: Jun. 6, 2024

(65) Prior Publication Data
US 2024/0320474 A1    Sep. 26, 2024

(30) Foreign Application Priority Data
Nov. 29, 2022  (CN) .......................... 202211506067.3

(51) Int. Cl.
*G06N 3/04*    (2023.01)
*G01D 18/00*   (2006.01)
(Continued)

(52) U.S. Cl.
CPC ......... *G06N 3/0455* (2023.01); *G01D 18/008* (2013.01); *G01N 33/02* (2013.01)

(58) Field of Classification Search
CPC ..... G06N 3/0455; G01D 18/008; G01N 33/02
(Continued)

(56) References Cited

U.S. PATENT DOCUMENTS

| 5,347,475 A | 9/1994 | Taylor et al. | |
| 2023/0091677 A1* | 3/2023 | Brown | G06N 20/00 |
| | | | 702/2 |
| 2023/0359889 A1* | 11/2023 | Berg | G06Q 50/02 |

FOREIGN PATENT DOCUMENTS

| CN | 106323909 A | 1/2017 |
| WO | 0169191 A1 | 9/2001 |
| WO | 2021191770 A1 | 9/2021 |

OTHER PUBLICATIONS

Gu Wen-Jun, et al., Characteristic Wavelength Selection Method of the Detection of Internal Quality of Blueberry Based on Hyperspectral Image, Journal of Shenyang Agricultural University, 2017, pp. 584-590, vol. 48, No. 5.

(Continued)

*Primary Examiner* — Aditya S Bhat
(74) *Attorney, Agent, or Firm* — Cooper Legal Group, LLC

(57) ABSTRACT

A photoelectric detection model transfer and sharing method and an Internet of Things monitoring and evaluation system based on a cloud service are provided. The transfer and sharing method includes: invoking a temperature compensation model and a spectrum transfer model to calibrate spectrum information of agricultural product samples, and invoking a detection model to compute the calibrated spectrum information to obtain detection results of the agricultural product samples. The Internet of Things monitoring and evaluation system calibrates spectrum information by (Continued)

using a spectrum transfer and sharing method, invokes a detection model for computing, and returns detection results to a detection terminal in real time, thereby realizing remote monitoring and evaluation of the quality of agricultural products.

5 Claims, 4 Drawing Sheets

(51) Int. Cl.
*G06N 3/0455* (2023.01)
*G01N 33/02* (2006.01)

(58) Field of Classification Search
USPC .......................................................... 702/77
See application file for complete search history.

(56) References Cited

OTHER PUBLICATIONS

Sun Jun, et al., Hyperspectral Detection of Moisture Content in Rice Based on MEA-BP Neural Network, Food Science, 2017, pp. 272-276, vol. 38, No. 10.

* cited by examiner

PHOTOELECTRIC DETECTION MODEL TRANSFER AND SHARING METHOD AND INTERNET OF THINGS MONITORING AND EVALUATION SYSTEM BASED ON CLOUD SERVICE

CROSS REFERENCE TO THE RELATED APPLICATIONS

This application is the national phase entry of International Application No. PCT/CN2022/140211, filed on Dec. 20, 2022, which is based upon and claims priority to Chinese Patent Application No. 202211506067.3, filed on Nov. 29, 2022, the entire contents of which are incorporated herein by reference.

TECHNICAL FIELD

The present disclosure relates to the field of quality grading and monitoring of agricultural products, and in particular, to a photoelectric detection model transfer and sharing method and an Internet of Things monitoring and evaluation system based on a cloud service.

BACKGROUND

With the upgrading of consumer demand, people pay more attention to the quality and safety of agricultural products after the demand for the quantity of agricultural products is satisfied. The agricultural products vary in quality among individuals due to their natural properties. Mixed sales can neither meet the multi-level demand preferences of consumers nor achieve higher prices for better quality of the agricultural products. Besides, it is more likely to cause vicious competition among enterprises in the environment of product homogeneity, which is not conducive to the healthy development of the entire agricultural product industry. Therefore, with the promotion of agricultural supply-side structural reform, the quality grading of agricultural products realizes quality-based pricing of agricultural products and meets the multi-level demand of consumers, which is of great significance to promote the effective supply and demand matching of agricultural products and reduce the waste of resources.

Spectrum analysis technologies have great advantages in internal quality detection of agricultural products. For example, the spectrum analysis technologies provide non-destructive and efficient detection, have low cost and good reproducibility, generally require no preprocessing for sample measurement, and are suitable for on-site detection and online analysis. A spectrum detection model between a spectrum matrix X and a response matrix Y needs to be built first for spectrum analysis. However, spectrums acquired by different spectrometers differ from each other due to the differences in the instruments, the aging of the instruments, the influences of environmental changes, or the like. A built quantitative analysis model faces the following challenges in practical application: (1) The analysis model built in one instrument cannot be used for a long time; (2) the analysis model built in one instrument cannot be directly used to perform quantitative analysis on a spectrum acquired by another instrument; (3) due to the toxicity, unstable chemical properties, high price, and the like of some samples, building a new model will cost a lot of manpower, material resources, and financial resources.

At present, the conventional agricultural product grading devices designed based on the spectrum analysis technologies are mostly online devices and can hardly meet the monitoring requirements. Besides, modeling for a single device wastes a lot of manpower and material resources. With the rise of the Internet of Things, big data, and cloud computing, spectrometers serving as a type of photoelectric sensors are a natural part of the Internet of Things. The combination of spectrum analysis technologies and information technologies realizes in-situ detection or monitoring of the quality of agricultural products and can be used by the national agricultural department, industry leaders, the national regulatory department, and so on. In addition, the Internet of Things makes it possible to share detection models and becomes an important driving force for the commercialization of detection devices.

With the development of the futures market, the varieties of futures in China become increasingly diversified and involve all the fields including agricultural products. For example, apple futures, listed and traded on the Zhengzhou Commodity Exchange, become the first fresh fruit futures both in China and the world. There are many reasons why China vigorously launches fruit futures, and the most important one is their attribute of "poverty alleviation". China is the world's largest producer and consumer of fruit, fruit is widely planted in China, and the output is large. The huge supply of fruit may easily cause the situation that farmers suffer a great loss due to low prices. Thanks to the listing of fruit futures, related enterprises, and growers can implement hedging, price discovery, and risk management as much as possible through apple futures. Meanwhile, the periodic and obvious fluctuation in the price of fruit and the large market scale of fruit make it possible to trade fruit as futures and are also important factors for the successful listing and stable operation of fruit futures in China. However, the degree of standardization of fruit futures is low at present. For example, the appearance of apples is not completely positively correlated with their internal quality, so that the apples are unqualified to be traded as standardized futures. Moreover, there is a big contradiction between the storability required by futures products and the intolerance to storage of fruit in stock.

To solve the problem of poor applicability of the spectrum detection model, ensure the quality of agricultural products, realize the rapid screening, detection, and evaluation of the quality and safety of agricultural raw materials and fruit during production and processing, and improve consumer confidence, it is necessary to develop a remote monitoring and evaluation system for the quality of agricultural products.

SUMMARY

To eliminate the defects in the prior art, the present disclosure provides a photoelectric detection model transfer and sharing method and an Internet of Things monitoring and evaluation system based on a cloud service, which realize remote sharing and update of a detection model, solve the problem of difficulty in monitoring the quality of agricultural products in the whole supply chain, and realize remote monitoring and evaluation of the quality of agricultural products.

The present disclosure achieves the above objective through the following technical means.

A photoelectric detection model transfer and sharing method based on a cloud service is provided, which includes:

acquiring in batches, by a detection terminal No. 0, spectrum information and temperature information of typical and representative agricultural product samples and building a temperature compensation model;

acquiring quality indicators of the typical and representative agricultural product samples, extracting characteristic wavelengths from a wavelength-calibrated spectrum, and building a detection model based on the characteristic wavelengths and the quality indicators;

acquiring in batches, by the detection terminal No. 0 and a detection terminal No. 1, the spectrum information of the typical and representative agricultural product samples and building a spectrum transfer model by using an autoencoder neural network;

invoking the temperature compensation model and the spectrum transfer model to calibrate the spectrum information of agricultural product samples, and invoking the detection model to compute the calibrated spectrum information to obtain detection results of the agricultural product samples.

Further, the process of building the spectrum transfer model by using the autoencoder neural network includes:

encoding, by an encoder, a spectrum matrix $S_1$ of the detection terminal No. 1 into a low-dimensional hidden variable h, restoring, by a decoder, the hidden variable h in a hidden layer to a spectrum matrix $S_0$ of the detection terminal No. 0, and learning, by the neural network, difference features between the matrix $S_0$ and the matrix $S_1$ and calibrating the matrix $S_1$ into the matrix $S_0$;

an encoding process from an input layer to the hidden layer being:

$$h = \theta_1(S_1) = w_1 X + b_1;$$

a decoding process from the hidden layer to an output layer being:

$$S_0 = \theta_2(h) = w_2 X + b_2,$$

where $w_1$ is a weight matrix of the encoding process, $w_2$ is a weight matrix of the decoding process, $\theta_1$ is a function of the encoding process, $\theta_2$ is a function of the decoding process, $b_1$ is a deviation matrix of the encoding process, $b_2$ is a deviation matrix of the decoding process, and X represents a spectrum matrix;

the spectrum transfer model includes an encoder and a decoder, the encoder includes the weight matrix $w_1$ and the deviation matrix $b_1$, and the decoder includes the weight matrix $w_2$ and the deviation matrix $b_2$.

The method further includes: when a new detection terminal is added, acquiring in small batches, by the new detection terminal, the spectrum information of the agricultural product samples and updating the spectrum transfer model by using a transfer learning method.

Further, the updating of the spectrum transfer model by using a transfer learning method includes: freezing parameter matrices of the autoencoder neural network updated by the detection terminal No. 0 and the detection terminal No. 1, adding a new decoder, and updating parameter matrices of the newly added decoder by the terminal No. 0 and the new detection terminal.

Further, serial numbers of the agricultural product samples are generated while the detection results are obtained, the samples are drawn according to the serial numbers for actual measurement, an error between the detection results and actual measurement results is computed, and if the error exceeds a preset threshold, the detection model is updated.

Further, the detection model is updated by using an active feedback mechanism and a passive feedback mechanism, where the active feedback mechanism includes: selecting representative agricultural product samples for active update of the detection model at key time points after harvesting, before storage, and before sale; and the passive feedback mechanism includes: during the detection process, numbering the samples required for detection, dynamically drawing a certain quantity of the samples as an independent validation set to validate the detection model, and if the error between the detection results and the actual measurement results exceeds the preset threshold, updating the model by using the independent validation set.

Further, the model update process includes: selecting representative agricultural product samples from the independent validation set and adding the selected samples into a training set of the built detection model.

Further, the wavelengths in the spectrum information acquired by the detection terminal are calibrated with a wavelength calibration equation.

Further, the wavelength calibration equation is acquired by: preselecting characteristic wavelengths with characteristic absorption peaks, acquiring a spectrum of a standard optical source by the detection terminal, and calibrating the characteristic wavelengths to obtain a wavelength calibration equation.

An Internet of Things monitoring and evaluation system is provided, which includes:

at least one detection terminal, configured to acquire information of agricultural product samples to be detected, the information including spectrum information, temperature information, and geographic information;

a data server, configured to calibrate the spectrum information by using a spectrum transfer and sharing method, invoke a detection model for computing, and return detection results to the detection terminal in real time, where the spectrum transfer and sharing method and the detection model are created with spectrum information of typical and representative agricultural product samples acquired in batches by the detection terminal, and the detection model is updated in real time with an active feedback mechanism and a passive feedback mechanism;

a cloud data management platform, configured to display the detection results, upload a spectrum transfer model and the detection model, perform user management, and control the detection terminal, where the detection terminal includes an optical source, sensors, a positioning module, and a control module, where the optical source is an active optical source provided for detecting the agricultural product samples; the sensors include a photoelectric sensor and a temperature sensor; the positioning module acquires geographic location information of the agricultural product quality detection terminal; and the control module controls the operation of the entire detection terminal and has photoelectric signal conversion, data display, and data transmission functions;

the detection terminal includes one or a combination of handheld, portable, vehicle-mounted, and online types.

The present disclosure has the following advantages. Compared with the prior art, the present disclosure provides a photoelectric detection model transfer and sharing method and an Internet of Things monitoring and evaluation system based on a cloud service.

(1) To solve the problem of poor applicability of the spectrum detection model, the present disclosure provides a photoelectric detection model transfer and sharing method based on a cloud service. According to the method, a temperature compensation model and a spectrum transfer model are invoked to calibrate the spectrum information of agricultural product samples, and a detection model is invoked to compute the calibrated spectrum information to obtain detection results of the agricultural product samples; therefore, the detection model can be used by different detection terminals.

(2) The present disclosure provides an Internet of Things monitoring and evaluation system, which includes a data server. The data server calibrates spectrum information by using a spectrum transfer and sharing method, invokes a detection model for computing, and returns detection results to a detection terminal in real time, thereby realizing remote monitoring and evaluation of the quality of agricultural products. The system can be widely applied in sampling inspection and evaluation of the quality of agricultural products.

BRIEF DESCRIPTION OF THE DRAWINGS

To illustrate the technical solutions in the embodiments of the present disclosure or in the prior art more clearly, the accompanying drawings required for the description of the embodiments or the prior art are introduced briefly in the following. Apparently, the accompanying drawings in the following description show merely some embodiments of the present disclosure, and persons of ordinary skill in the art can derive other drawings from the accompanying drawings without creative efforts.

DETAILED DESCRIPTION OF THE EMBODIMENTS

In order to make the objectives, technical solutions, and advantages of the present disclosure clearer, the technical solutions of the present disclosure will be clearly described below with reference to the accompanying drawings in the embodiments of the present disclosure. It is obvious that the embodiments to be described are only a part rather than all of the embodiments of the present disclosure. All other embodiments derived by persons of ordinary skill in the art based on the embodiments of the present disclosure without creative efforts shall fall within the protection scope of the present disclosure.

Figure 1:
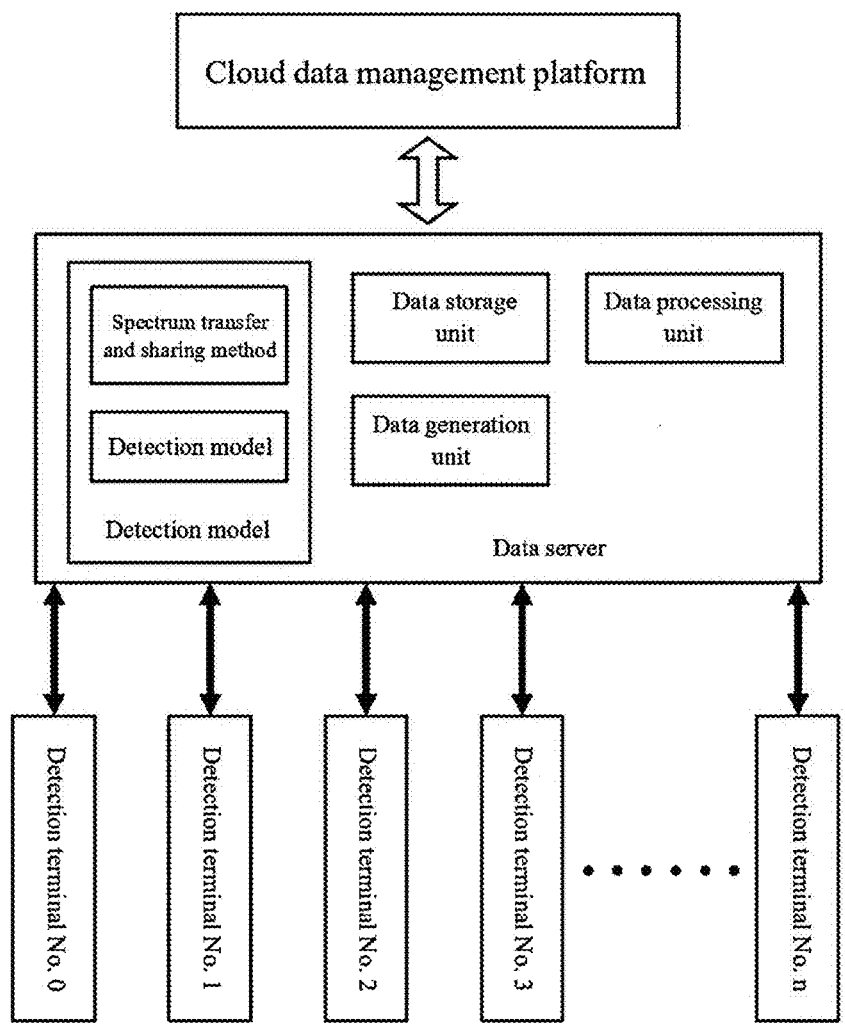
FIG. 1 is a schematic structural diagram of an Internet of Things monitoring and evaluation system based on a cloud service according to the present disclosure.

The present disclosure provides an Internet of Things monitoring and evaluation system. As shown in FIG. 1, the system consists of at least one detection terminal, a data server, and a cloud data management platform. The detection terminal acquires information of agricultural product samples to be detected and wirelessly uploads the information to the data server. The data server calibrates spectrum information by using a spectrum transfer and sharing method, invokes a detection model for computing, returns detection results to a display screen of the detection terminal in real time, and sends the detection results to the cloud data management platform at the same time. The spectrum transfer and sharing method and the detection model are created with the spectrum information of typical and representative agricultural product samples acquired in batches by the detection terminal. The detection model is updated in real time with an active feedback mechanism and a passive feedback mechanism. The system realizes in-situ real-time detection, monitoring, and evaluation of the quality of agricultural products.

The detection terminal includes an optical source, sensors, a positioning module, a wireless communication module, a control module, a display screen, and a power source, and is configured to sense the spectrum information about the quality of agricultural products.

Further, the control module controls the operation of the entire detection terminal and has functions such as photoelectric signal conversion, data display, and data transmission. The optical source is a halogen lamp or a light-emitting diode (LED) which is an active optical source provided for detecting the agricultural product samples. The sensors include a photoelectric sensor and a temperature sensor. The photoelectric sensor is configured to acquire the spectrum information of the agricultural products irradiated by the optical source. The temperature sensor is configured to sense the temperature of the agricultural products. The control module transmits the information acquired by the sensors to the data server. The data server calibrates the spectrum information to meet the application requirements in multiple scenarios. The positioning module is configured to acquire geographic location information of the agricultural product quality detection terminal, the control module sends the location information to the data server, and the data server combines the location information with the detection results (for example, soluble solid content) of the detection model to realize visual evaluation and display of the quality of agricultural products in the production areas. The wireless communication module is configured to wirelessly transmit data, including the spectrum information and the data acquired by the positioning module, to realize interaction between the control module and the data server. The display screen is connected to the control module and is configured to display related information of the detection terminal such as the serial number of the detection terminal, the temperature of agricultural products, the detection results, and the network connection status. The power source is a rechargeable battery enabling each component of the detection terminal to work for a long time.

Further, the detection terminal includes one or a combination of handheld, portable, vehicle-mounted, and online types, which meet the detection and monitoring requirements in multiple scenarios such as agricultural product harvesting, warehousing, logistics, raw material sampling inspection, and shelf-life quality evaluation.

The data server includes a data storage unit, a data processing unit, a data generation unit, and an execution unit, and is configured to perform data processing on the spectrum information acquired by the detection terminal.

Further, the wireless communication module wirelessly transmits the acquired spectrum information, temperature information, and location information to the data storage unit. The data processing unit processes the spectrum information and the temperature information. Specifically, the data processing unit calibrates the spectrum information with a temperature compensation model and a spectrum transfer model and invokes the detection model for computing. The data generation unit generates tables and graphics based on the data processed by the data processing unit, uploads the tables and graphics to the cloud data management platform for management personnel to view, manage, and evaluate, and generates serial numbers of the agricultural product samples at the same time. The management personnel draw samples according to the serial numbers for actual measurement, and import actual measurement results into the data processing unit for error computing, which is used for the update of the detection model.

The cloud data management platform is configured to display the results and control the detection terminal, and includes one or more of computer display terminals, mobile phone display terminals, and flat-panel display terminals.

Figure 2:
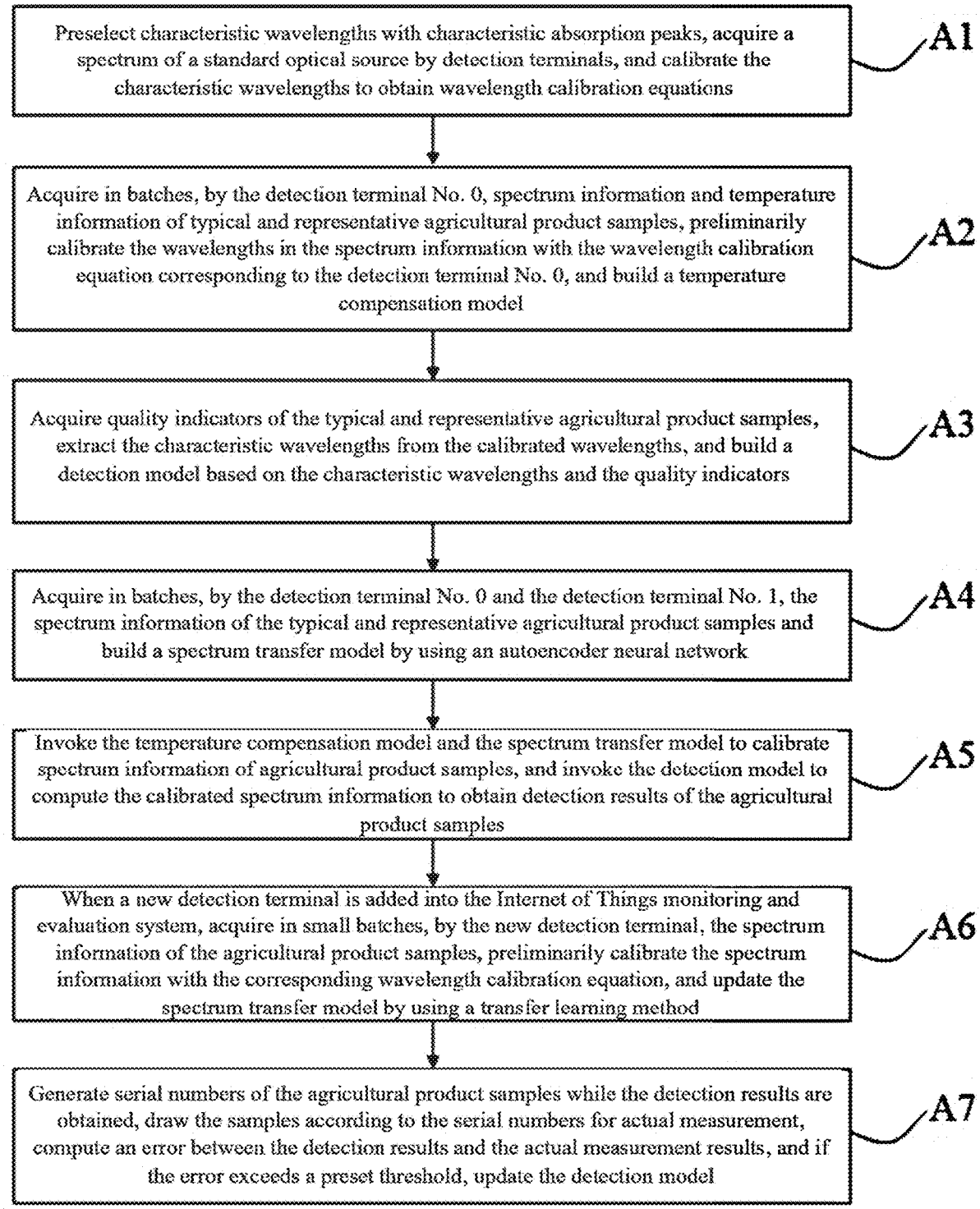
FIG. 2 is a flowchart of a photoelectric detection model transfer and sharing method based on a cloud service according to the present disclosure.

The present disclosure provides a photoelectric detection model transfer and sharing method based on a cloud service. As shown in FIG. 2, the method includes the following steps.

A1: Characteristic wavelengths with characteristic absorption peaks are preselected, a spectrum of a standard optical source is acquired by the detection terminals, and the characteristic wavelengths are calibrated to obtain wavelength calibration equations.

A2: The spectrum information and temperature information of typical and representative agricultural product samples are acquired in batches by the detection terminal No. 0, the wavelengths in the spectrum information are preliminarily calibrated with the wavelength calibration equation corresponding to the detection terminal No. 0, and a temperature compensation model is built.

A3: Quality indicators, such as soluble solid content, hardness, and acidity, of the typical and representative agricultural product samples are acquired, where the soluble solid content is measured by a refractometer, the hardness is measured by a physical property meter, and the acidity is measured by a pH meter, the characteristic wavelengths are extracted from the wavelength-calibrated spectrum, and a detection model is built based on the characteristic wavelengths and the quality indicators.

A4: The spectrum information of the typical and representative agricultural product samples is acquired in batches by the detection terminal No. 0 and the detection terminal No. 1, where the spectrum information acquired by the detection terminal No. 1 needs to be calibrated with the corresponding wavelength calibration equation, and a spectrum transfer model is built by using an autoencoder neural network.

A5: The spectrum transfer model, the temperature compensation model, and the detection model are uploaded by a computer to the data server, the temperature compensation model and the spectrum transfer model are invoked to calibrate the spectrum information of the agricultural product samples, and the detection model is invoked to compute the calibrated spectrum information to obtain detection results (that is, quality results) of the agricultural product samples.

A6: When a new detection terminal is added into the Internet of Things monitoring and evaluation system, the spectrum information of the agricultural product samples is acquired in small batches by the new detection terminal, then preliminarily calibrated with a corresponding wavelength calibration equation, and sent to the computer; the spectrum transfer model is updated by using a transfer learning method and is again uploaded to the data server to improve its generalization performance.

A7: The serial numbers of the agricultural product samples are generated while the detection results are obtained, the samples are drawn according to the serial numbers for actual measurement, and the actual measurement results are imported into the data processing unit to compute an error between the detection results and the actual measurement results, and if the error exceeds a preset threshold, the detection model is updated.

In the step A1, the calibration range is 400 nm to 2500 nm, and the wavelength calibration equation is $Y=a_1x^1+a_2x^2+\ldots+a_nx^n+b$, where Y represents calibrated wavelengths, $a_1, a_2, \ldots, a_n$ represent calibration coefficients, $x^1, x^2, \ldots, x^n$ represent preselected characteristic wavelengths, and b is a constant.

In the step A2, the detection terminal No. 0 acquires the spectrum information of the typical and representative agricultural product samples by diffuse transmission or diffuse reflection; and the temperature compensation model for the agricultural products to be detected is built by one or a combination of orthogonal signal correction, dynamic orthogonal projection, and external parameter orthogonalization.

In the step A3, the characteristic wavelengths are extracted by using one or a combination of genetic optimization algorithm, joint interval algorithm, simulated annealing algorithm, ant colony optimization algorithm, and competitive adaptive reweighted sampling algorithm.

Optionally, the detection model includes a quantitative prediction model or a qualitative discrimination model. The one or more quality indicators of the agricultural products to be detected are, for example, one or more of soluble solid content, hardness, acidity, and vitamin C content of apples, or one or more of moisture content, fatty acid, and reducing sugar of rice. Each of the quality indicators corresponds to one quantitative prediction model or qualitative discrimination model. The detection model for the quality of agricultural products to be detected is built by using one or a combination of multiple linear regression, partial least squares, artificial neural network, principal component analysis, and support vector machine, and the building process is described in the prior art. The detection model can be customized.

In the process of building the detection model, before the characteristic wavelengths are extracted, a total reflection spectrum and a dark noise spectrum are automatically calibrated and converted into an absorbance spectrum, where the total reflection spectrum is acquired and stored by the photoelectric sensor in advance and the dark spectrum is acquired and stored by the photoelectric sensor when the optical source is turned off. The absorbance spectrum is further calibrated by using a preprocessing method to remove intervals, with signal-to-noise ratios being lower than a preset signal-to-noise ratio, at two ends of the absorbance spectrum. The calibrated absorbance spectrum is randomly divided into a training set and a test set at a ratio of 3:1. The preprocessing method includes one or a combination of smoothing, multiplicative scatter correction, standard normal transformation, first derivative, and second derivative.

Figure 3:
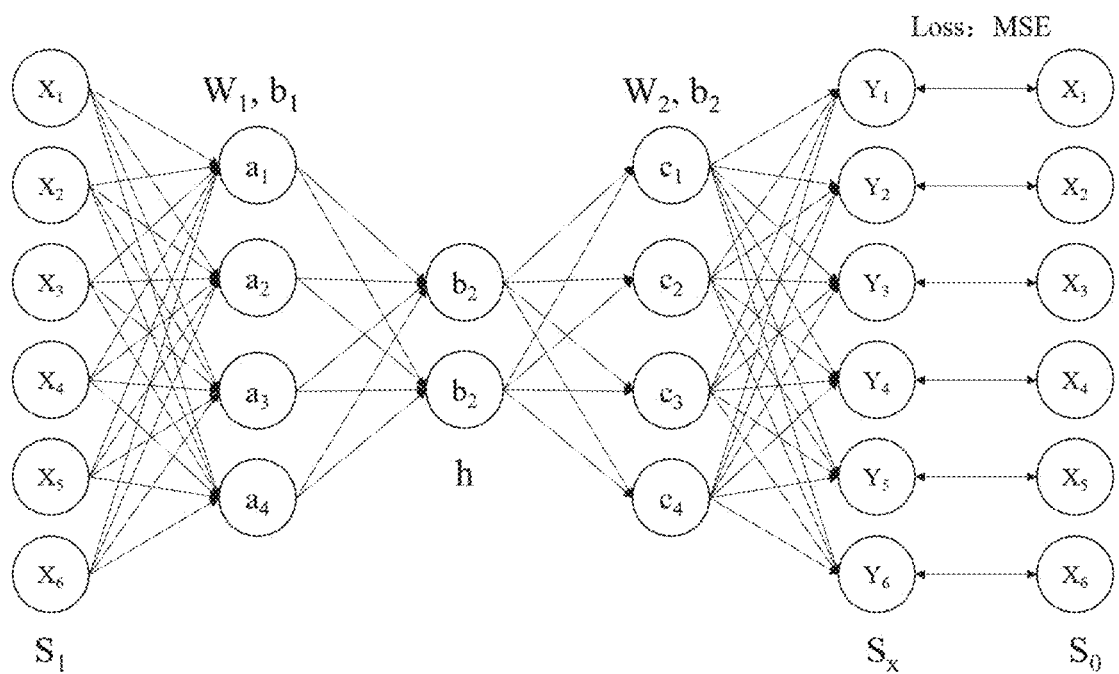
FIG. 3 is a schematic diagram of an autoencoder neural network for building a spectrum transfer model according to the present disclosure.

In the step A4, the process of building the spectrum transfer model by using the autoencoder neural network is as follows: Referring to FIG. 3, an encoder encodes a spectrum matrix $S_1$ (consisting of the detected spectrum information) of the detection terminal No. 1 into a low-dimensional hidden variable h, a decoder restores the hidden variable h in a hidden layer to a spectrum matrix $S_0$ of the detection terminal No. 0, and the neural network learns the difference features between the matrix $S_0$ and the matrix $S_1$ and calibrates the matrix $S_1$ into the matrix $S_0$.

The encoding process from an input layer to the hidden layer is:

$$h = \theta_1(S_1) = w_1 X + b_1;$$

the decoding process from the hidden layer to an output layer is:

$$S_0 = \theta_2(h) = w_2 X + b_2,$$

where $w_1$ is a weight matrix of the encoding process, $w_2$ is a weight matrix of the decoding process, $\theta_1$ is a function of the encoding process, $\theta_2$ is a function of the decoding process, $b_1$ is a deviation matrix of the encoding process, $b_2$ is a deviation matrix of the decoding process, and X represents a spectrum matrix.

Therefore, the spectrum transfer model includes an encoder and a decoder, the encoder includes the weight matrix $w_1$ and the deviation matrix $b_1$, and the decoder includes the weight matrix $w_2$ and the deviation matrix $b_2$.

In the step A6, the process of updating the spectrum transfer model by using the transfer learning method is as follows: The parameter matrices (including the weight matrices and the deviation matrices) of the autoencoder neural network that are updated by the detection terminal No. 0 and the detection terminal No. 1 are frozen. A new decoder is added and the parameter matrices of the newly added decoder are updated by the terminal No. 0 and the new detection terminal. The robustness of the spectrum transfer model can be enhanced in the presence of only a small number of samples, and the model can be used by different detection terminals.

In the step A7, the detection model is updated by using the active feedback mechanism and the passive feedback mechanism as follows: Typical and representative agricultural product samples are selected for active update of the detection model at key time points after harvesting, before storage, and before sale. During the detection process, the samples required for detection are numbered, and a certain quantity (greater than or equal to 30) of the samples are dynamically drawn as an independent validation set to validate the detection model. If the error between the detection results and the actual measurement results exceeds the preset threshold, the passive feedback is activated and the system management personnel are informed, and passive update of the model is carried out by using the independent validation set.

Further, the model update process is as follows: Representative agricultural product samples are selected from the independent validation set and added into the training set of the built detection model to expand the original sample coverage and variation range of the detection model, thereby improving the adaptability of the detection model and its prediction accuracy of new product samples.

Apple futures are taken as an example in this embodiment. The photoelectric detection model transfer and sharing method and the Internet of Things monitoring and evaluation system based on a cloud service are used to acquire in batches near-infrared spectrum data sets representing quality information of apples, and build an apple quality detection model and a spectrum transfer and sharing method to realize quality monitoring and evaluation of apples in different production areas.

Figure 4:
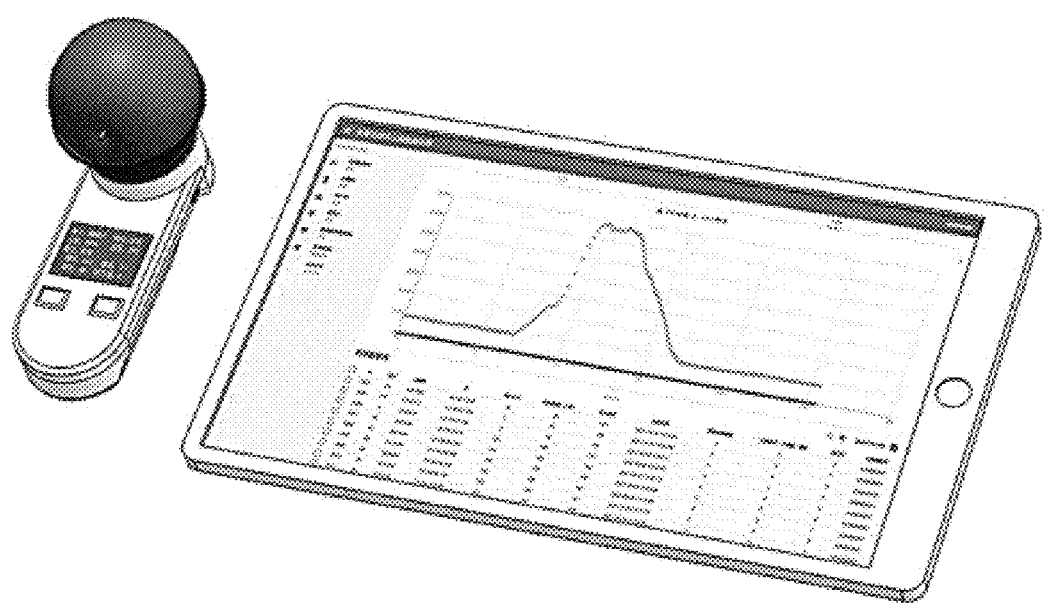
FIG. 4 is a schematic diagram of a handheld detection terminal and a data management platform according to the present disclosure.

The hardware of the handheld detection terminal mainly consists of a wide-spectrum LED optical source, a near-infrared photoelectric sensor, a temperature sensor, a rechargeable lithium battery, a display screen, a control circuit, a shading ring, a rubber gasket, and a housing. As shown in FIG. 4, a built-in positioning module is configured to acquire geographic location information of the apple production area; a 4G/5G module for wireless data transmission is configured to send the data to the data storage unit and the data processing unit of the cloud server; the photoelectric detection model transfer and sharing method and the detection model are invoked for spectrum calibration and result computing; after the detection is completed, the detection results are returned to the display screen of the handheld detection terminal and are sent to the cloud data management platform at the same time.

Multiple handheld detection terminals are taken as an example in this embodiment, and the detection model transfer and sharing method is performed in the following steps:

A1: Five fixed wavelengths with characteristic absorption peaks are preset, the calibration range is 400 nm to 1100 nm, the spectrum of a mercury-argon standard optical source is acquired by the detection terminals, and the fixed wavelengths are calibrated to obtain wavelength calibration equations.

The wavelength calibration equation of the detection terminal No. 0 is:

$$F_0(x) = 0.00001615x^3 - 0.03863x^2 + 31.67x - 8089;$$

the wavelength calibration equation of the detection terminal No. 1 is:

$$F_1(x) = 0.00001364x^3 - 0.03228x^2 + 26.34x - 6597;$$

the wavelength calibration equation of the detection terminal No. 2 is:

$$F_2(x) = 0.00001526x^3 - 0.03542x^2 + 35.71x - 8161.$$

A2: The diffuse reflection spectrum information and temperature information of typical and representative apple samples to be detected are acquired by the detection terminal No. 0, the wavelengths are preliminarily calibrated with the wavelength calibration equation of the detection terminal No. 0, and a temperature compensation model is built by using an external parameter orthogonalization method.

The external parameter orthogonalization method is based on principal component analysis to reduce the spatial dimensions of external parameters. The spectrum information of the apple samples to be detected is projected into the orthogonal space by using the external parameter orthogonalization method to filter out interference information. The details are as follows:

The spectrum matrix X can be expressed as:

$$X = X_p + X_q + R,$$

where $X_p$ is a projection matrix of the useful part, $X_q$ is a projection matrix of the useless part (influenced by temperature), and R is a redundant matrix.

$X_p$ is computed as follows: (1) The spectrum information of the typical and representative apple samples to be detected is collected and a spectrum matrix $X_i$ is obtained, where $X_i$ is a matrix consisting of n×m dimensional spectrums and i=1, 2, . . . , p represents different temperature levels. (2) A mean spectrum $x_i$ of i matrices is computed, where $x_i$ is the mean value of the spectrums of all the apple samples to be detected at different temperature levels, $x_i$ is a row vector with a row number of 1, and the number of columns is m. (3) $d_i=x_i-x_j$ is calculated, where j is one of 1, 2, . . . , p and serves as a reference temperature, and $d_1$, $d_2$, . . . , $d_p$ are combined into a differential spectrum matrix D in order. (4) A covariance matrix of D is computed and singular value decomposition is performed, that is, SVD $(D^T D)$-USV$^T$, to obtain a singular matrix V. (5) A subset $V_s$ of the matrix V is formed with the first c columns of V and the redundant parts are filtered out. In principle, the singular values of the first c columns account for more than 99% of the total values. (6) The projection matrix of the useless part $X_q=V_s V_S^T$ is computed and the projection matrix of the useful part $X_p$=IQ is computed, where I is an identity matrix.

A3: The quality indicators of the typical and representative apple samples are acquired, the characteristic wavelengths are extracted from the wavelength-calibrated spectrum, and a detection model is built based on the characteristic wavelengths and the quality indicators.

The soluble solid content of apples is measured by a refractometer, 26 characteristic wavelengths are extracted by using a competitive adaptive reweighted sampling algorithm, and a partial least squares (PLS) quantitative prediction model is built based on the soluble solid content and the 26 characteristic wavelengths. The details are as follows:

$$y = 30485x_1 + 2.1243x_2 + 0.6999x_3 - 0.7435x_4 - 1.8286x_5 - \\ 2.5479x_6 - 2.5548x_7 - 2.7023x_8 - 2.2712x_9 - 1.6531x_{10} - 0.2221x_{11} + \\ 0.0235x_{12} + 0.2166x_{13} + 0.5907x_{14} + 0.5023x_{15} - 0.0463x_{16} - \\ 0.5329x_{17} + 0.1552x_{18} + 0.4554x_{19} + 1.1918x_{20} + 2.0570x_{21} + \\ 1.8016x_{22} + 1.3537x_{23} + 0.0881x_{24} + 1.5010x_{25} + 2.3522x_{26} + 5.0562,$$

where y is a predicted value of the detection model and x represents the extracted characteristic wavelength values.

A4: The spectrum information of the typical and representative apple samples to be detected is acquired in batches by the detection terminal No. 0 and the detection terminal No. 1, where the spectrum information acquired by the detection terminal No. 1 needs to be calibrated with the corresponding wavelength calibration equation. A spectrum transfer model is built by using the autoencoder neural network, where the encoder encodes a spectrum matrix $S_1$ of the detection terminal No. 1 into a low-dimensional hidden variable h, and the decoder restores the hidden variable h in a hidden layer to a spectrum matrix $S_0$ of the detection terminal No. 0, and the neural network learns the difference features between the matrix $S_0$ and the matrix $S_1$ and calibrates $S_1$ into $S_0$.

A5: The spectrum transfer model, the temperature compensation model, and the detection model are uploaded to the cloud server, the spectrum information of apples to be detected is acquired by the detection terminals, the temperature compensation model and the spectrum transfer model are invoked to calibrate the spectrum, the detection model is invoked to compute the calibrated 26 characteristic wavelengths, and the detection results are returned in real time to the display screens of the detection terminals.

A6: The spectrum information of the apple samples to be detected is acquired in small batches by the detection terminal No. 2 and is calibrated with the corresponding wavelength calibration equation. The detection model is constantly updated by using the transfer learning method, and the generalization performance of the spectrum transfer model is improved.

A7: When the sampling inspection is performed by the detection terminal No. 2 on the apples, the apple samples to be detected are numbered. An independent sample set for sampling inspection is set to 30, and the data generation unit automatically generates 30 serial numbers. Users perform actual measurement on the soluble solid content of the apples according to the corresponding serial numbers and upload the measurement results. The data processing unit computes the error, and if the error exceeds a preset threshold, the detection model is automatically updated; otherwise, the model is continuously used.

Although the embodiments of the present disclosure have been described above with reference to the accompanying drawings, persons skilled in the art can still make various modifications and variations without departing from the spirit and scope of the present disclosure. Such modifications and variations shall fall within the scope defined by the appended claims.

What is claimed is:

1. A photoelectric detection model transfer and sharing method based on a cloud service, comprising:
acquiring in batches, by a detection terminal No. 0, spectrum information and temperature information of typical and representative agricultural product samples and building a temperature compensation model;
acquiring quality indicators of the typical and representative agricultural product samples, extracting characteristic wavelengths from a wavelength-calibrated spectrum, and building a detection model based on the characteristic wavelengths and the quality indicators;
acquiring in batches, by the detection terminal No. 0 and a detection terminal No. 1, the spectrum information of the typical and representative agricultural product samples and building a spectrum transfer model by using an autoencoder neural network, wherein the acquiring in batches, by the detection terminal No. 0 and the detection terminal No. 1, comprises measuring the spectrum information acquired by the detection terminal No. 0 and the detection terminal No. 1 with an optical source and a photoelectric sensor of the detection terminal No. 0 and with an optical source and a photoelectric sensor of the detection terminal No. 1, wherein the spectrum information measured by the detection terminal No. 0 is provided in a spectrum matrix $S_0$, the spectrum information measured by the detection terminal No. 1 is provided in a spectrum matrix $S_1$, wherein the building the spectrum transfer model comprises training the autoencoder neural network on difference features between the spectrum matrix $S_0$ and the spectrum matrix $S_1$ and calibrating the spectrum matrix $S_1$ into the spectrum matrix $S_0$; and invoking the temperature compensation model and the spectrum transfer model to calibrate spectrum information of agricultural product samples to yield calibrated spectrum information, and invoking the detection model to compute the calibrated spectrum information to obtain quality detection results of the agricultural product samples, wherein the building the spectrum transfer model comprises:

encoding, by an encoder, the spectrum matrix $S_1$ of the detection terminal No. 1 into a low-dimensional hidden variable h, restoring, by a decoder, the low-dimensional hidden variable h in a hidden layer of the spectrum matrix $S_0$ of the detection terminal No. 0, and the training the autoencoder neural network on the difference features between the spectrum matrix $S_0$ and the spectrum matrix $S_1$ and the calibrating the spectrum matrix $S_1$ into the spectrum matrix $S_0$;

an encoding process from an input layer to the hidden layer being:

$$h = \theta_1(S_1) = w_1 X + b_1;$$

a decoding process from the hidden layer to an output layer being:

$$S_0 = \theta_2(h) = w_2 X + b_2,$$

wherein $w_1$ is a weight matrix of the encoding process, $w_2$ is a weight matrix of the decoding process, $\theta_1$ is a function of the encoding process, $\theta_2$ is a function of the decoding process, $b_1$ is a deviation matrix of the encoding process, $b_1$, is a deviation matrix of the decoding process, and X represents a spectrum matrix;

the spectrum transfer model comprises the encoder and the decoder, the encoder comprises the weight matrix $w_1$ and the deviation matrix $b_1$, and the decoder comprises the weight matrix $w_2$ and the deviation matrix $b_2$, further comprising: when a new detection terminal is added, acquiring the spectrum information of the agricultural product samples by the new detection terminal, and updating the spectrum transfer model by using a transfer learning method, to enhance a robustness of the spectrum transfer model and realize the spectrum transfer model sharing in different detection terminals, wherein the updating the spectrum transfer model by using the transfer learning method comprises: freezing parameter matrices of the autoencoder neural network updated by the detection terminal No. 0 and the detection terminal No. 1, adding a new decoder, and updating parameter matrices of the new decoder by the detection terminal No. 0 and the new detection terminal, wherein serial numbers of the agricultural product samples are generated while the detection results are obtained, the agricultural product samples are drawn according to the serial numbers for actual measurement, an error between the detection results and actual measurement results is computed, and when the error exceeds a preset threshold, the detection model is updated, wherein the detection model is updated by using an active feedback mechanism and a passive feedback mechanism, wherein the active feedback mechanism comprises: selecting representative agricultural product samples for active update of the detection model at key time points after harvesting, before storage, and before sale; and the passive feedback mechanism comprises: during a detection process, numbering the agricultural product samples required for detection, dynamically drawing a certain quantity of the agricultural product samples as an independent validation set to validate the detection model, and when the error between the detection results and the actual measurement results exceeds the preset threshold, updating the detection model by using the independent validation set, wherein the updating the model comprises: selecting representative agricultural product samples from the independent validation set to obtain selected samples and adding the selected samples into a training set of the detection model, thereby improving an adaptability of the detection model and a prediction accuracy of the detection model for new product samples.

2. The photoelectric detection model transfer and sharing method according to claim 1, wherein wavelengths in the spectrum information acquired by the detection terminal are calibrated with a wavelength calibration equation.

3. The photoelectric detection model transfer and sharing method according to claim 2, wherein the wavelength calibration equation is acquired by: preselecting characteristic wavelengths with characteristic absorption peaks, acquiring a spectrum of a standard optical source by the detection terminal, and calibrating the characteristic wavelengths with characteristic absorption peaks to obtain a wavelength calibration equation.

4. An Internet of Things monitoring and evaluation system, comprising:

a plurality of detection terminals configured to acquire information of agricultural product samples to be detected, the information comprising spectrum information, temperature information, and geographic information, wherein the plurality of detection terminals are each configured to measure the spectrum information with a respective optical source and a respective photo electric sensor and wherein each of the plurality of detection terminals comprises one or a combination of handheld, portable, vehicle-mounted, and online types;

a data server, configured to calibrate the spectrum information by performing a spectrum transfer and sharing method, invoke a detection model for computing, and return detection results to a corresponding one of the plurality of detection terminals in real time, wherein the spectrum transfer and sharing method and the detection model are created with spectrum information of typical and representative agricultural product samples acquired in batches by the corresponding one of the plurality of detection terminals, and the detection model is updated in real time with an active feedback mechanism and a passive feedback mechanism, wherein the spectrum information measured by a first detection terminal of the plurality of detection terminals is provided in a spectrum matrix $S_0$ and the spectrum information measured by a second detection terminal of the plurality overdetection terminals is provided in a spectrum matrix $S_1$, and wherein the spectrum transfer and sharing method comprises training an autoencoder neural network on difference features between the spectrum matrix $S_0$ and the spectrum matrix $S_1$ and calibrating the spectrum matrix $S_1$ into the spectrum matrix $S_0$; and a cloud data management platform, configured to display detection results and control each of the plurality of detection terminals.

5. The Internet of Things monitoring and evaluation system according to claim 4, wherein the plurality of detection terminals each comprise sensors, a positioning module, and a control module, wherein the optical source is an active optical source provided for detecting the agricultural product samples; the sensors comprise the photoelectric sensor and a temperature sensor; the positioning module acquires geographic location information of the corresponding one of the plurality of detection terminals; and the control module controls operation of the corresponding one of the plurality of detection terminals and has photoelectric signal conversion, data display, and data transmission functions.

* * * * *